(12) United States Patent
Frandsen, Jr. et al.

(10) Patent No.: US 9,626,752 B2
(45) Date of Patent: Apr. 18, 2017

(54) METHOD AND APPARATUS FOR IC 3D LEAD INSPECTION HAVING COLOR SHADOWING

(71) Applicant: Delta Design, Inc., Poway, CA (US)

(72) Inventors: Walter James Frandsen, Jr., Ramona, CA (US); Kexiang Ken Ding, San Diego, CA (US)

(73) Assignee: Delta Design, Inc., Poway, CA (US)

( * ) Notice: Subject to any disclaimer, the term of this patent is extended or adjusted under 35 U.S.C. 154(b) by 234 days.

(21) Appl. No.: 14/283,466

(22) Filed: May 21, 2014

(65) Prior Publication Data
US 2014/0347446 A1    Nov. 27, 2014

Related U.S. Application Data

(60) Provisional application No. 61/826,327, filed on May 22, 2013.

(51) Int. Cl.
| | |
|---|---|
| *H04N 13/04* | (2006.01) |
| *H04N 9/47* | (2006.01) |
| *G06T 7/00* | (2017.01) |
| *G01B 11/02* | (2006.01) |
| *G01N 21/88* | (2006.01) |
| *G01N 21/95* | (2006.01) |
| *G01N 21/956* | (2006.01) |

(52) U.S. Cl.
CPC ............ *G06T 7/0004* (2013.01); *G01B 11/02* (2013.01); *G01N 21/8806* (2013.01); *G01N 21/95* (2013.01); *G01N 21/95684* (2013.01); *G06T 2207/10024* (2013.01); *G06T 2207/30148* (2013.01)

(58) Field of Classification Search
CPC ......... G06T 7/0004; G06T 2207/10024; G06T 2207/30148; G01B 11/02; G01N 21/88
USPC ......................................... 348/46, 86–88, 92
See application file for complete search history.

(56) References Cited

U.S. PATENT DOCUMENTS

| | | | | |
|---|---|---|---|---|
| 6,005,965 A | * | 12/1999 | Tsuda ............... | G01N 21/95684 250/559.08 |
| 2008/0013158 A1 | * | 1/2008 | Shires .............. | G01N 21/95684 359/299 |
| 2013/0120557 A1 | * | 5/2013 | King .................. | G01N 21/8806 348/92 |

* cited by examiner

*Primary Examiner* — Andy Rao
*Assistant Examiner* — Jared Walker
(74) *Attorney, Agent, or Firm* — Foley & Lardner LLP

(57) ABSTRACT

A system for three-dimensional inspection of leads mounted on an integrated circuit device includes an integrated circuit device, a first light source having a first color, a second light source having a second color different from the first color, a RGB color camera and a processor. The first light source is disposed at an acute angle to the integrated circuit device, and is configured to illuminate the leads such that lead shadows are created in a first color plane. The second light source is disposed in front of a surface of the integrated circuit device on which the leads are mounted, and is configured to illuminate the leads in a second color plane. The camera is configured to image the illuminated leads and lead shadows. The processor is configured to analyze the first and second color planes of a single image to detect three-dimensional bent leads.

17 Claims, 6 Drawing Sheets

METHOD AND APPARATUS FOR IC 3D LEAD INSPECTION HAVING COLOR SHADOWING

CROSS-REFERENCE TO RELATED APPLICATIONS

This application claims the benefit under 35 U.S.C. §119 (e) of U.S. Provisional Application No. 61/826,327, filed on May 22, 2013, the contents of which are hereby incorporated by reference in their entirety into the present disclosure.

FIELD OF THE INVENTION

The present invention relates generally to a device inspection system, and more particularly to a color shadowing system for inspecting leads of an IC package, particularly for leaded devices such as quad flat packages ("QFP"), thin small-outline packages ("TSOP") and other types of IC packages.

BACKGROUND

Manufacturers process and test semiconductor or integrated circuit ("IC") devices using various types of automated machinery. Before IC devices are shipped to wholesalers or consumers, they are usually tested for performance and inspected for physical defects. One physical defect that is important to identify is the presence of bent leads on leaded devices such as quad flat packages ("QFP"), thin small-outline packages ("TSOP") and other types of IC packages.

Generally, mechanical systems or basic camera systems are employed to identify bent leads. However, current mechanical and camera systems are limited in their ability to detect bent leads accurately. In one conventional mechanical system, 3D lead inspection is performed by placing the IC device on a pedestal in front of a camera to ensure a lighting angle pattern. However, placing the IC device on the pedestal makes the inspection slower. In a second type of conventional mechanical system, an interferometer is used to create interference patterns on the IC device leads. To obtain the required resolution, the camera must take multiple images or use different angles of lights to get the 3D lead information of the IC device. This also slows down the inspection process. In a third type of conventional mechanical system, a laser generates an angular projected pattern on the IC device leads. Use of the laser to generate a 3D profile slows down the inspection process and increases the space requirements. In a fourth type of conventional mechanical system, a side view prism views the leads from a side and projects side view images on a front view image. However, the setup is complicated and expensive. In addition, the inspected device must be stopped in front of the camera's field of view. In many cases, the device has to be inserted into a prism fixture to obtain side view images.

Therefore, it would be desirable to provide a reliable, accurate and relatively quicker (i.e., on the fly) 3D lead inspection imaging apparatus capable of accurately detecting bent leads on a leaded device such as a QFP, a TSOP, or any other type of surface mount IC package using a single image to obtain 3D lead information.

SUMMARY

According to one embodiment, an integrated inspection system for three-dimensional inspection of leads of an integrated circuit device includes an integrated circuit device, a first light source having a first color, a second light source having a second color different from the first color, a color camera and a processor. The integrated circuit device includes a plurality of leads mounted on the integrated surface device. The first light source is disposed at an acute angle with respect to the integrated circuit device, and is configured to illuminate the leads such that light emitted from the first light source creates lead shadows of the plurality of leads in the first color image plane of the color camera. The second light source is disposed in front of a surface of the integrated circuit device on which the leads are mounted. The second light source is configured to illuminate the leads in the second color image plane of the color camera. The color camera is configured to image the different color illuminated leads and the lead shadows of the integrated circuit device in the corresponding color image planes. The processor is coupled to the camera, and is configured to analyze the corresponding color image planes of a single color image captured by the color camera to detect three-dimensional bent lead defects in the leads mounted on the integrated circuit device.

According to another embodiment, an imaging apparatus for three-dimensional inspection of leads mounted on an integrated circuit device includes a first light source having a first color, a second light source having a second color different from the first color, a color camera and a processor. The first light source is disposed at an acute angle with respect to the integrated circuit device, and is configured to illuminate the leads such that light emitted from the first light source creates lead shadows of the plurality of leads in the first color image plane of the color camera. The second light source is disposed in front of a surface of the integrated surface device on which the leads are mounted. The second light source is configured to illuminate the leads in the second color image plane of the color camera. The color camera is configured to image the different color illuminated leads and the lead shadows of the integrated circuit device in the corresponding color image planes. The processor is coupled to the camera, and is configured to analyze the corresponding color image planes of a single color image captured by the camera to detect three-dimensional bent lead defects in the leads mounted on the integrated circuit device.

According to another embodiment, a method for three-dimensional inspection of leads of an integrated circuit device includes illuminating a plurality of leads mounted on an integrated circuit device with a first light source having a first color, the first light source disposed at an acute angle with respect to the integrated circuit device such that light emitted from the first light source creates lead shadows of the plurality of leads in the first color image plane of a color camera. The method further includes illuminating the plurality of leads of the integrated circuit device with a second light source having a second color different from the first color, the second light source disposed in front of a surface of the integrated circuit device on which the leads are mounted, imaging the illuminated leads in the second color image plane of the color camera of the integrated circuit device with the color camera, and analyzing the corresponding color image planes of a single color image captured by the color camera with a processor to detect three-dimensional bent lead defects in the leads mounted on the integrated circuit device.

It is to be understood that both the foregoing general description and the following detailed description are exemplary and explanatory only, and are not restrictive of the invention as claimed. These and other features, aspects and advantages of the present invention will become apparent from the following description, appended claims, and the accompanying exemplary embodiments shown in the drawings, which are briefly described below.

DETAILED DESCRIPTION

Embodiments of the present invention will be described below with reference to the accompanying drawings. It should be understood that the following description is intended to describe exemplary embodiments of the invention, and not to limit the invention. The invention can be used for any inspections with shadowing like lead inspections for leaded devices such as quad flat packages ("QFP"), thin small-outline packages ("TSOP") and other type of surface mount IC package. Generally, IC inspection systems carry out a number of individual tests on each IC device during and after the manufacturing process.

Figure 1:
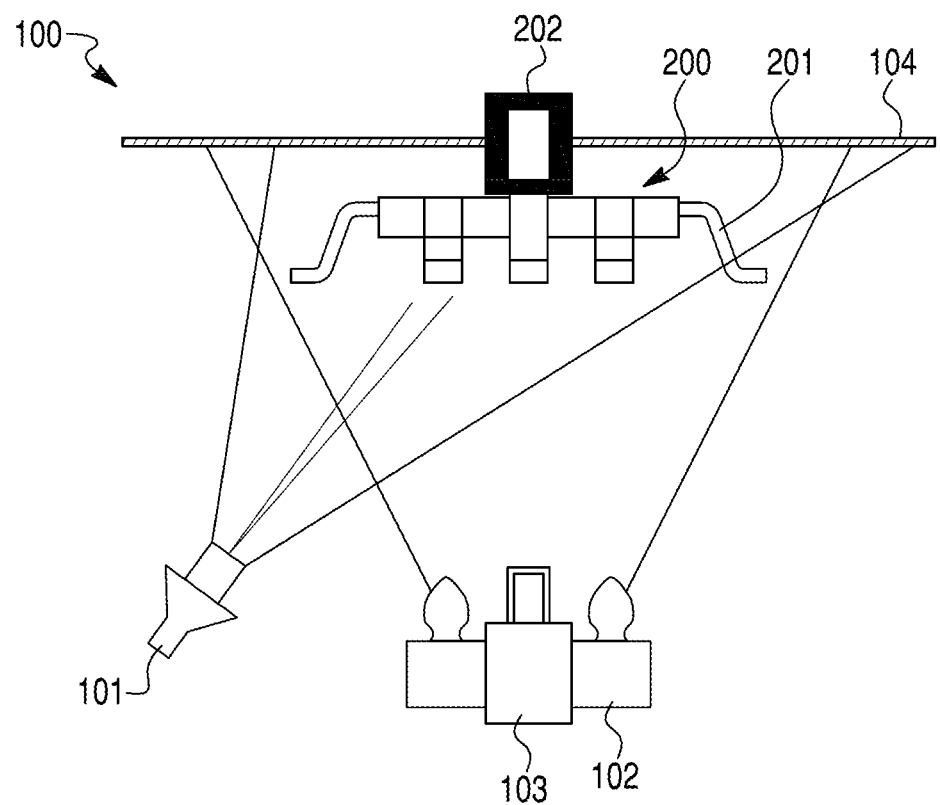
FIG. 1 is a side view of a color imaging apparatus in the corresponding color image planes with color shadowing for IC 3D lead inspection, according to one embodiment.

Referring now to FIG. 1, an imaging apparatus 100 configured to perform IC 3D lead inspection with color shadowing includes a first LED 101, a second LED 102 and a color camera 103. To perform IC 3D lead inspection with the color imaging apparatus 100, an IC device 200 is placed in front of a background 104 to improve contrast. The background 104 may be, for example, a white background. The IC device 200 includes a plurality of leads 201 mounted on the IC device 200. The plurality of leads 201 include a plurality of flat leads 201A and a plurality of gull wing leads 201B (see FIG. 3). A nozzle 202 is provided and configured to hold the IC device 200.

The first LED 101 has a first color and the second LED 102 has a second color, different from the first color. In this embodiment, the first LED 101 is a red LED and the second LED 102 is a blue LED. Using red and blue LEDs allows for a larger separation in wavelength. In other embodiments, the first LED 101 may be blue, while the second LED 102 may be red. One of ordinary skill in the art will appreciate that any different color LEDs may be used for the first LED 101 and the second LED 102, provided that the first LED 101 and the second LED 102 are not the same color, and are therefore, capable of separating the lead shadows and the 2D leads. The separation process will be discussed in further detail below. While LEDs may be employed, other sources may be used to perform the IC 3D lead inspection, provided that the lead shadows produced are measurable with the light source.

In this example, the camera 103 is a RGB color camera capable of producing three color image planes (i.e., red, blue and green) per each image captured. The red and blue image planes are used to separate the lead shadows and the 2D leads. Alternatively, the green image plane of the color camera may be used instead of either the red or blue image planes of the camera 103.

To create lead shadows on the background 104, the first LED 101 is disposed at an acute angle to the IC device 200 and illuminates the leads 201 of the IC device 200 in a first color image plane. For example, the acute angle may be 45 degrees. The optical axis of the camera 103 is aligned perpendicularly with respect to a surface of the IC device 200 on which the leads 201 are mounted. The second LED 102 is disposed in front of the surface of the IC device 200 on which the leads 201 are mounted and illuminates the leads 201 of the IC device 200 in a second color image plane. In this embodiment, the first color image plane is a red image plane and the second color image plane is a blue image plane.

Figure 2B:
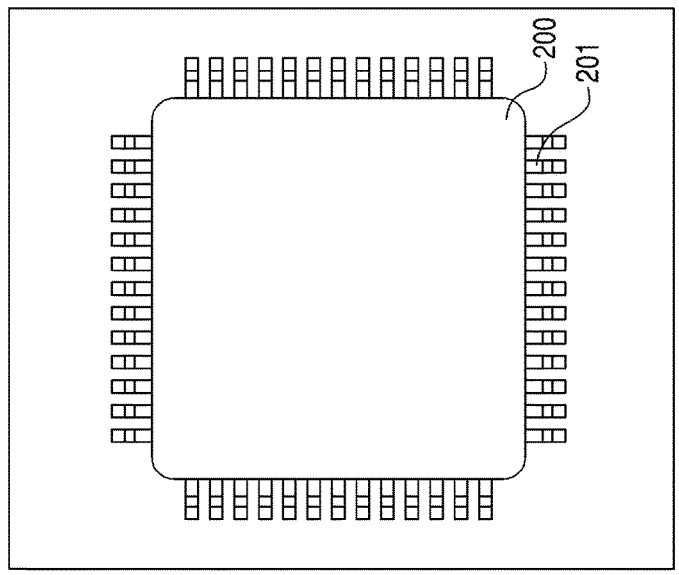
FIGS. 2A and 2B are images illustrating lead shadows and 3D lead information in the corresponding color image planes acquired by the color imaging apparatus of FIG. 1.
Figure 2A:
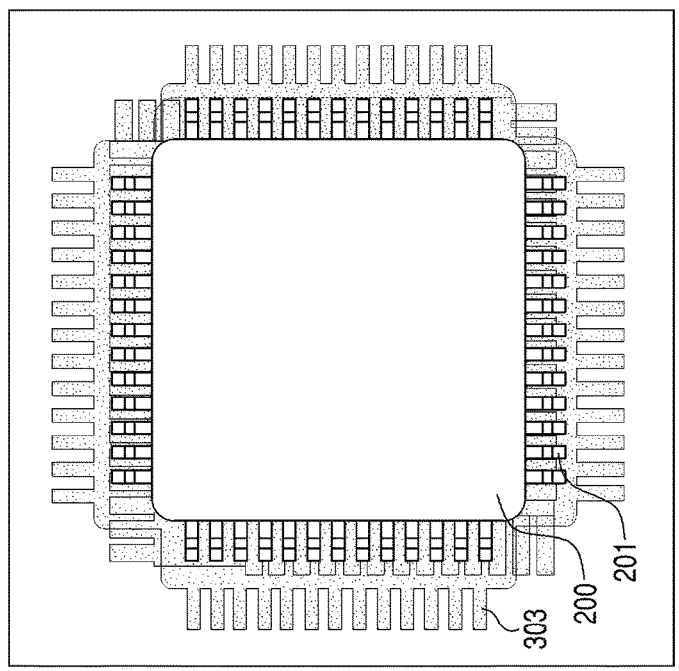

Referring now to FIG. 2, in order to perform IC 3D lead inspection, a microprocessor extracts information from the red image plane and the blue image plane of a single shot (e.g., a RGB color image) captured by the color camera 103 to generate color images 301 and 302. Color image 301 illustrates the 2D leads and the lead shadows 303 produced by the first LED 101, while color image 301 illustrates the 2D leads. The lead shadow in the color image 301 is defined as a difference between a length of the 2D lead and lead shadow 303 of the color image 301 and a length of the 2D lead of the color image 302.

Figure 4:
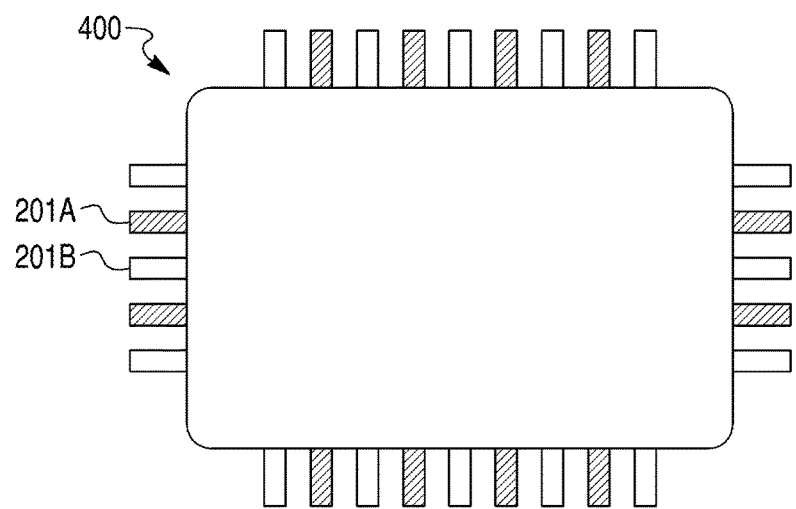
FIG. 4 is a bottom view of the calibration target in a second color image plane of a color camera of FIG. 3.

Prior to performing IC 3D lead inspection, the imaging apparatus 100 is calibrated using a calibration target 400, as illustrated in FIG. 4. The calibration method will be discussed in further detail below. During lead calibration, a calibrated lead shadow 304 is measured. During operation of the imaging apparatus 100, if a lead shadow 303 of a lead 201 is longer than the calibrated lead shadow 304 for the corresponding lead in the calibration target 400, the lead 201 is bent away from the background 104 (i.e. away from the back of the IC device 200). If the lead shadow 303 of the lead 201 is shorter than the calibrated lead shadow 304, the lead 201 is bent closer to the background 104 (i.e. toward the back of the IC device 200). Bent leads are longer or shorter in x and y directions as compared to straight leads.

The imaging apparatus 100 can determine how much (i.e., an extent to which), if any, a lead 201 is bent and in which direction the lead 201 is bent, based on a single image captured by the camera 103, which contains information regarding the red, blue and green image planes.

Lead Calibration

Figure 3:
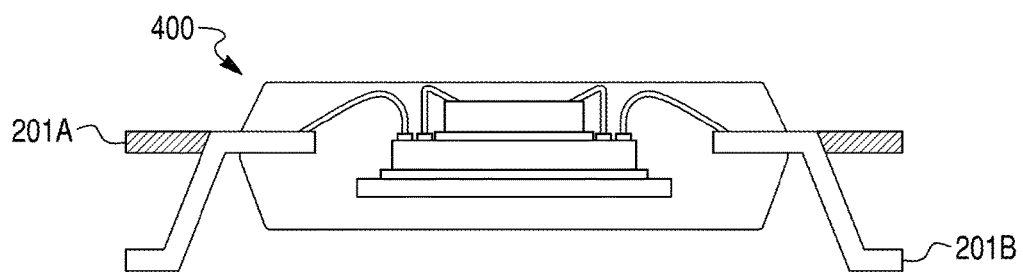
FIG. 3 is a cross sectional view of a calibration target used to calibrate the imaging apparatus of FIG. 1.
Figure 5:
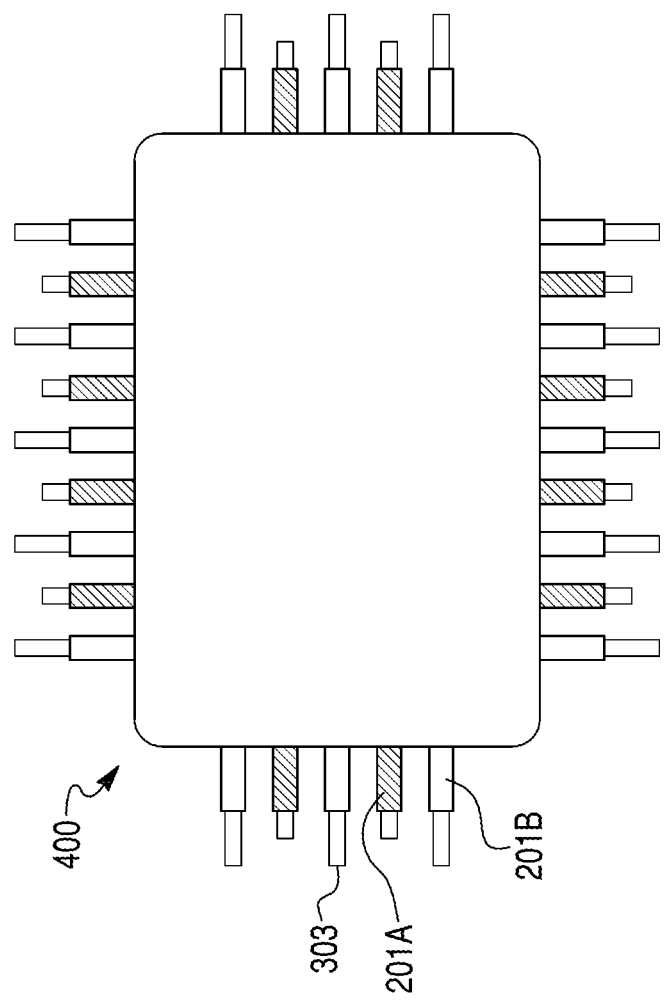
FIG. 5 is a bottom view of the calibration target leads in a first color image plane of a color camera of FIG. 3 including lead shadows produced by the imaging apparatus of FIG. 1.

To correlate the shadow change to the bent lead in z direction, a calibration target 400 is used. Referring now to FIGS. 3-5, the flat leads 201A and the gull wing leads 201B are mounted around a circumference of the calibration target 400. Although not illustrated, the imaging apparatus 100 is used to measure a length of a calibrated lead shadow 304 corresponding to the flat leads 201A and the gull wing leads 201B of the calibration target 400. Specifically, the camera 103 may be used to capture a single image of the calibration target 400. Using a single captured image from the camera, the microprocessor can extract information from a first color image plane (e.g., the red color image plane) to generate a first color image 301 that illustrates the 2D leads and lead shadows 303 of the calibration target 400. Using the same single captured image, the microprocessor can also extract information from a second color image plane (e.g., the blue color image plane) to generate a second color image 302 that illustrates the 2D leads. By comparing the differences in length of the leads 201 in the first and second color images 301 and 302, a length of a calibrated lead shadow 304 corresponding to each lead 201A and 201B of the calibration target 400 can be measured.

Since the z distances of the flat leads 201A and the gull wing leads 201B are known, a shadow measurement of the lead shadows 303 can be used to determine the amount of lead bending in the z direction.

Method for 3D Lead Inspection of Leads of an IC Device

Figure 6:
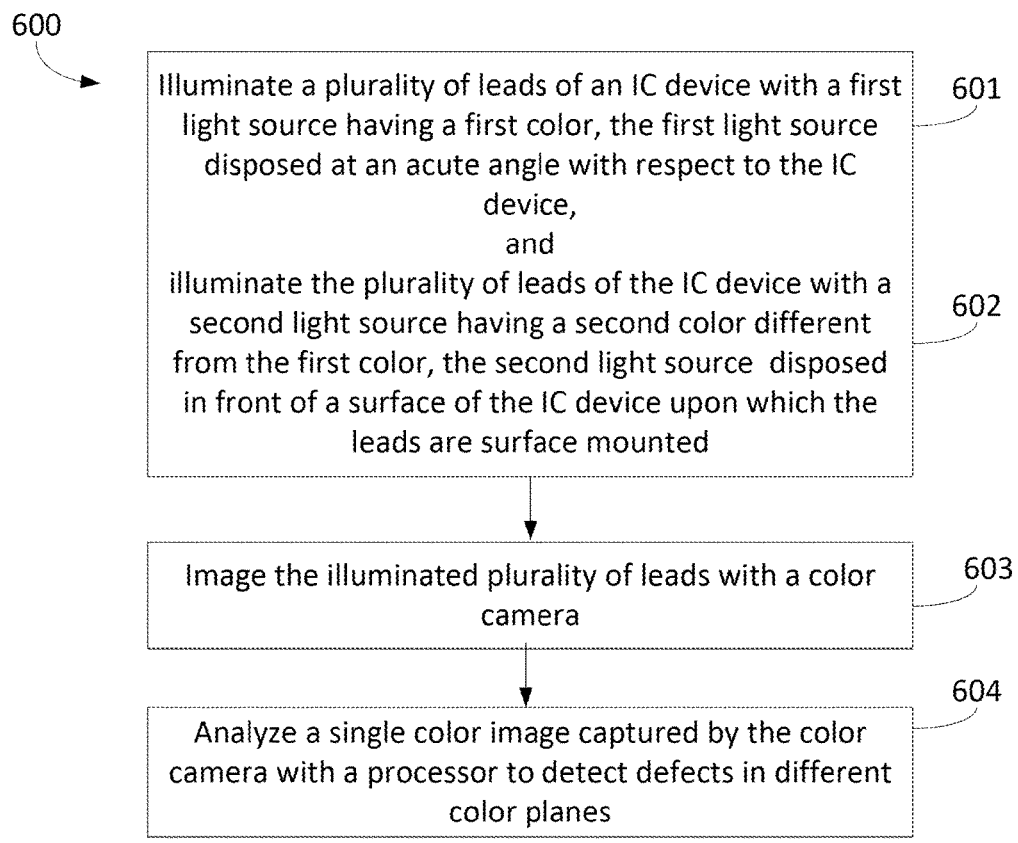
FIG. 6 is an example process for performing 3D lead inspection of leads of an IC device with the color imaging apparatus of FIG. 1.

Referring to FIG. 6, a process 600 for performing 3D lead inspection of leads of an IC device is described. First, the first LED 101 is disposed at an acute angle to the IC device 200 and illuminates the leads 201 of the IC device 200 such that light emitted from the first LED 101 creates lead shows of the leads 201 (Step 601). The second LED 102 is disposed in front of the surface of the IC device 200 upon which the leads 201 are mounted, and illuminates the leads 201 of the IC device 200 (Step 602). As seen in FIG. 6, Steps 601 and 602 occur at the same time. In other words, the leads 201 are illuminated by the first LED 101 and the second LED 102 at the same time. Then, the camera 103 (i.e., a color camera) captures images of the IC device 200, including the illuminated leads 201, on the fly (Step 603). The information captured by the imaging apparatus 100 is analyzed by a microprocessor (not shown) running software for processing visual images captured during IC device 200 inspection, and the microprocessor detects the extent to which, if any, the leads 201 are defective (Step 604). In particular, in Step 604, a single color image captured by the color camera is analyzed with a processor to detect defects in different color planes.

Figure 7:
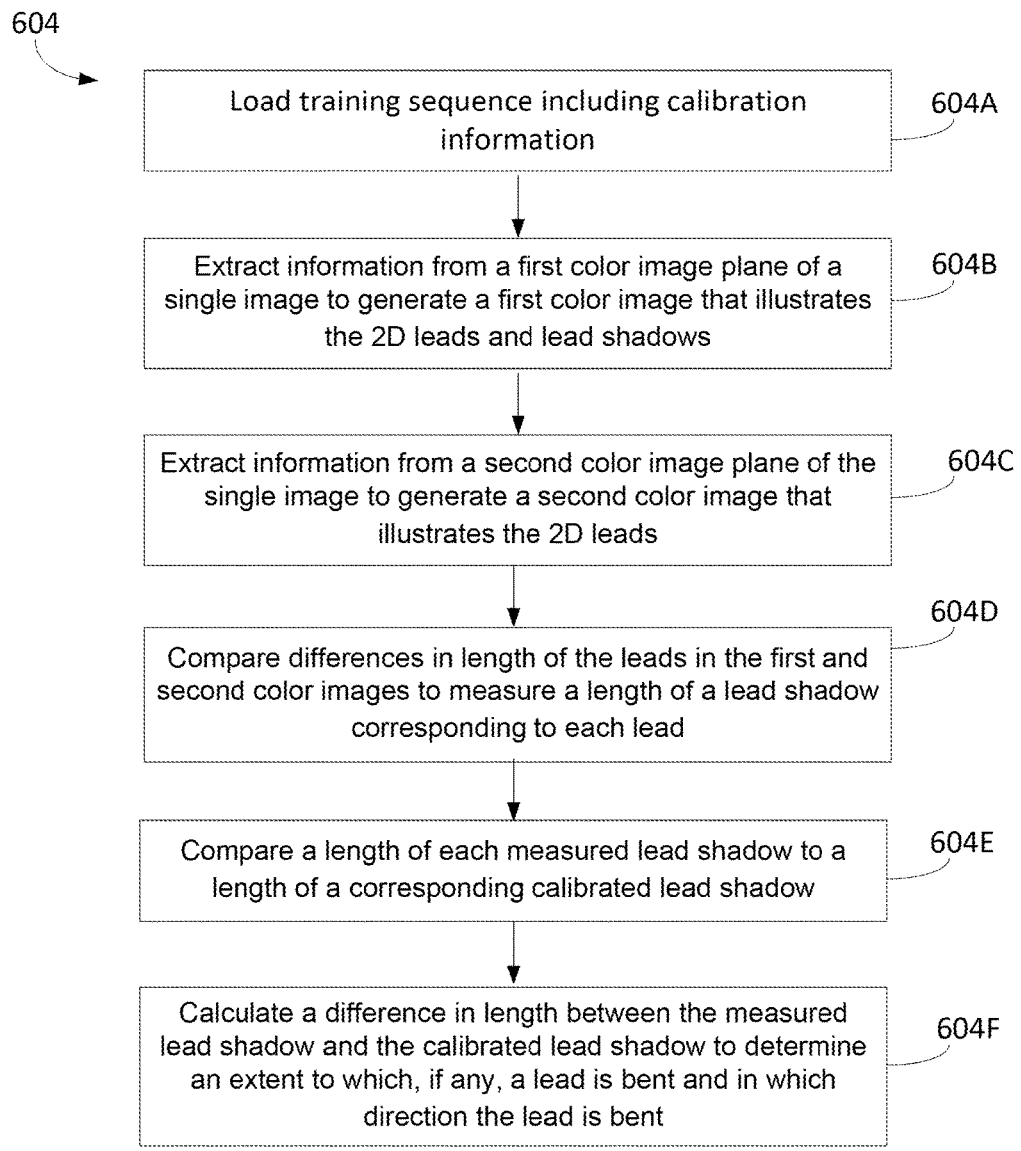
FIG. 7 is an example process for analyzing an image in the corresponding color image planes captured by a color camera in the process of FIG. 6 to detect three-dimensional bent lead defects.

Referring to FIG. 7, the analyzing Step 604 by which the microprocessor detects defects in the leads 201 is described in further detail. First, the microprocessor loads a training sequence including the information acquired during the manual and/or automatic lead calibration performed with the calibration target 400 (Step 604A). Using a single captured color image, the microprocessor can extract information from a first color image plane (e.g., the red color image plane) to generate a first color image 301 that illustrates the 2D leads and lead shadows 303 (Step 604B). Using the same single captured color image, the microprocessor can also extract information from a second color image plane (e.g., the blue color image plane) to generate a second color image 302 that illustrates the 2D leads (Step 604C). The microprocessor then compares the differences in length of the leads 201 in the first and second color image planes 301 and 302 to measure a length of a lead shadow 303 corresponding to each lead 201 (Step 604D).

The microprocessor then compares the length of each measured lead shadow 303 to a length of a corresponding calibrated lead shadow 304 (Step 604E). The microprocessor calculates the difference in length between the measured lead shadow 303 and the calibrated lead shadow 304 to determine an extent to which a lead 201 is bent and in which direction the lead 201 is bent (Step 604F). In particular, if a lead shadow 303 is longer than the calibrated lead shadow 304, the microprocessor determines that the lead 201 is bent away from the background 104. If the lead shadow 303 is shorter than the calibrated lead shadow 304, the microprocessor determines that the lead 201 is bent closer to the background 104.

According to certain aspects of the invention, certain advantages are realized. For example, color image shadows may be used to determine an extent to which the leads 201 are bent and in which direction the lead 201 is bent in three-dimensional coordinates. Unlike the conventional inspection systems described in the background, the imaging apparatus 100 is capable of using a single image captured by the camera 103 with on the fly imaging to perform the 3D lead measurement and inspection. An inspection method utilizing the imaging apparatus 100 is fast and cost-effective in that on-the-fly imaging can be performed with a simple camera and LED lights.

The training sequence described above is exemplary. One of ordinary skill in the art will appreciate that the training sequence can also be separated to three separate sequences, such as setup with detailed parameter settings, training for getting image templates, calibration for determining the pixel scale, etc. In addition, the imaging apparatus 100 can be used as a standalone vision inspection system or integrated vision inspection system on testing handlers.

Although the present invention has been described in reference to a particular embodiment, various other embodiments and modifications will be apparent to those skilled in the art. It is therefore intended that the foregoing description of a preferred embodiment be considered as exemplary only.

What is claimed is:

1. An integrated inspection system for three-dimensional inspection of leads of an integrated circuit device, the integrated inspection system comprising:
    an integrated circuit device comprising a plurality of leads mounted on the integrated circuit device;
    a first light source having a first color, the first light source disposed at an acute angle with respect to the integrated circuit device, and configured to illuminate the leads such that light emitted from the first light source creates lead shadows of the leads in a first color image plane;
    a second light source having a second color different from the first color, the second light source disposed in front of a surface of the integrated circuit device on which the leads are mounted, and configured to illuminate the leads in a second color image plane;
    a RGB color camera configured to image the illuminated leads and lead shadows in the first and second color image planes of a color image of the integrated circuit device; and
    a processor coupled to the camera, the processor configured to analyze the first and second color image planes of a single RGB color image captured by the RGB color camera to detect three-dimensional bent lead defects in the leads mounted on the integrated circuit device,
    wherein the processor uses information from the first color image plane to generate a first image illustrating the leads in two dimensions and the lead shadows, and
    wherein the processor uses information from the second color image plane to generate a second image illustrating the leads in two dimensions, and
    wherein the processor compares a length of a two-dimensional lead and a lead shadow thereof from the first image with a length of a corresponding two-dimensional lead from the second image to determine a length of the lead shadow for each of the leads.

2. The integrated inspection system according to claim 1, wherein an optical axis of the camera is perpendicular to the surface of the integrated circuit device on which the leads are mounted.

3. The integrated inspection system according to claim 1, wherein the first color is red and the second color is blue.

4. The integrated inspection system according to claim 1, wherein the first color is blue and the second color is red.

5. The integrated inspection system according to claim 1, further comprising a calibration target comprising a plurality of leads mounted on the calibration target, the calibration target configured to be illuminated by the first light source such that the microprocessor is capable of measuring a length of a calibrated lead shadow for each of the leads of the calibration target.

6. The integrated inspection system according to claim 5, wherein the microprocessor compares the length of each lead shadow in the first image with a length of a corresponding calibrated lead shadow of the calibration target to determine an extent to which the lead mounted on the integrated circuit device is bent.

7. The integrated inspection system according to claim 5, wherein if the length of the lead shadow is longer than the length of the calibrated lead shadow, the microprocessor determines that the lead is bent away from a back surface of the integrated circuit device, and if the length of the lead shadow is shorter than the length of the calibrated lead shadow, the microprocessor determines that the lead is bent toward the back surface of the integrated circuit device.

8. The integrated inspection system according to claim 1, wherein the camera is configured to image the illuminated leads of the integrated circuit device on the fly.

9. An imaging apparatus for three-dimensional inspection of leads mounted on an integrated circuit device, the imaging apparatus comprising:
   a first light source having a first color, the first light source disposed at an acute angle with respect to the integrated circuit device, and configured to illuminate the leads such that light emitted from the first light source creates lead shadows of the leads in a first color image plane;
   a second light source having a second color different from the first color, the second light source disposed in front of a surface of the integrated surface device on which the leads are mounted, and configured to illuminate the leads in a second color image plane;
   a RGB color camera configured to image the illuminated leads and lead shadows in the first and second color image planes of a color camera image of the integrated circuit device; and
   a processor coupled to the camera, the processor configured to analyze the first and second color image planes of a single RGB color image captured by the RGB color camera to detect three-dimensional bent lead defects in the leads mounted on the integrated circuit device,
   wherein the processor uses information from the first color image plane to generate a first image illustrating the leads in two dimensions and the lead shadows, and wherein the processor uses information from the second color image plane to generate a second image illustrating the leads in two dimensions, and
   wherein the processor compares a length of a two-dimensional lead and a lead shadow thereof from the first image with a length of a corresponding two-dimensional lead from the second image to determine a length of the lead shadow for each of the leads.

10. The imaging apparatus according to claim 9, wherein the first color is red and the second color is blue.

11. The imaging apparatus according to claim 9, wherein the first color is blue and the second color is red.

12. A method for three-dimensional inspection of leads of an integrated circuit device, the method comprising:
   illuminating a plurality of leads mounted on an integrated circuit device with a first light source having a first color, the first light source disposed at an acute angle with respect to the integrated circuit device such that light emitted from the first light source creates lead shadows of the leads in a first color image plane;
   illuminating the leads with a second light source having a second color different from the first color, the second light source disposed in front of a surface of the integrated circuit device on which the leads are mounted, and configured to illuminate the leads in a second color image plane;
   imaging the illuminated leads of the integrated circuit device with a camera;
   analyzing a single image captured by the camera with a processor to detect defects in the leads mounted on the integrated circuit device;
   using information from the first color image plane to generate, with the processor, a first image illustrating the leads in two dimensions and the lead shadows;
   using information from the second color image plane to generate, with the processor, a second image illustrating the leads in two dimensions; and
   comparing a length of a two-dimensional lead and a lead shadow thereof from the first image with a length of a corresponding two-dimensional lead from the second image to determine a length of the lead shadow for each of the leads.

13. The method of claim 12, wherein the first color is red and the second color is blue.

14. The method of claim 12, wherein the first color is blue and the second color is red.

15. The method of claim 12, further comprising:
   calibrating a calibration target by illuminating a plurality of leads mounted on the calibration target with a first light source disposed at an acute angle with respect to the calibration target such that light emitted from the first light source creates lead shadows of the leads;
   illuminating the leads of the calibration target with a second light source disposed in front of a surface of the calibration target on which the leads are mounted;
   imaging the illuminated leads of the integrated circuit device with a camera; and
   analyzing a single image captured by the camera with a processor to measure a length of a calibrated lead shadow for each of the leads of the calibration target.

16. The method of claim 15, wherein the microprocessor compares the length of each lead shadow in the first image with a length of a corresponding calibrated lead shadow of the calibration target to determine an extent to which the lead of the integrated circuit device is bent.

17. The method of claim 16, wherein if the length of the lead shadow is longer than the length of the calibrated lead shadow, the microprocessor determines that the lead is bent away from a back surface of the integrated circuit device, and if the length of the lead shadow is shorter than the length of the calibrated lead shadow, the microprocessor determines that the lead is bent toward the back surface of the integrated circuit device.

* * * * *